(12) United States Patent
Lin et al.

(10) Patent No.: US 9,462,957 B2
(45) Date of Patent: Oct. 11, 2016

(54) PORTABLE ELECTROCARDIOGRAPHY DEVICE

(71) Applicant: IMEC Taiwan Co., Hsinchu (TW)

(72) Inventors: Ting Cheng Lin, Tainan (TW); Svend Larsen, Hsinchu (TW); Peter Lemmens, Tao-Yuan (TW)

(73) Assignee: IMEC Taiwan Co., Hsinchu (TW)

( * ) Notice: Subject to any disclaimer, the term of this patent is extended or adjusted under 35 U.S.C. 154(b) by 86 days.

(21) Appl. No.: 14/080,915

(22) Filed: Nov. 15, 2013

(65) Prior Publication Data

US 2014/0142411 A1 May 22, 2014

Related U.S. Application Data

(60) Provisional application No. 61/727,418, filed on Nov. 16, 2012.

(51) Int. Cl.
*A61B 5/0416* (2006.01)
*A61B 5/0404* (2006.01)
*A61B 5/00* (2006.01)
*A61B 5/0408* (2006.01)

(52) U.S. Cl.
CPC ......... *A61B 5/0416* (2013.01); *A61B 5/04085* (2013.01); *A61B 5/0006* (2013.01); *A61B 5/0404* (2013.01); *A61B 5/0408* (2013.01); *A61B 2560/0431* (2013.01)

(58) Field of Classification Search
CPC .............. A61B 5/0006; A61B 5/0408; A61B 5/04085; A61B 5/6831; A61B 5/404; A61B 5/0416; A61B 2560/0431; A61N 1/39; A61N 1/3993
USPC .................................................. 600/508, 509
See application file for complete search history.

(56) References Cited

U.S. PATENT DOCUMENTS

| | | | |
|---|---|---|---|
| 4,112,941 A | * | 9/1978 | Larimore ....................... 600/394 |
| 2002/0072682 A1 | * | 6/2002 | Hopman et al. .............. 600/509 |
| 2005/0251003 A1 | * | 11/2005 | Istvan et al. .................. 600/393 |
| 2006/0068649 A1 | * | 3/2006 | Silber ........................... 439/835 |
| 2010/0069981 A1 | * | 3/2010 | Vaisnys .................... A61N 1/39 607/6 |

* cited by examiner

*Primary Examiner* — Christopher D Koharski
*Assistant Examiner* — Pamela M Bays
(74) *Attorney, Agent, or Firm* — McDonnell Boehnen Hulbert & Berghoff LLP

(57) ABSTRACT

A portable electrocardiography (ECG) device includes a first pair of first type snap-in buttons at a first plane of a case. The first type snap-in buttons are configured for coupling to ECG electrodes having a second type snap-in button. The portable ECG device also includes a processor in electrical connection with the first pair of first type snap-in buttons. The processor is configured for monitoring and processing electrocardiography signals obtained by the ECG electrodes.

16 Claims, 8 Drawing Sheets

PORTABLE ELECTROCARDIOGRAPHY DEVICE

CROSS REFERENCE TO RELATED APPLICATION

The present application claims the benefit of priority of U.S. Provisional Patent Application Ser. No. 61/727,418 filed on Nov. 16, 2012, the contents of which are hereby incorporated by reference.

FIELD

The present invention generally relates to an electrical measuring device and, more particularly, to a portable electrocardiography device.

BACKGROUND

An electrocardiography (ECG) device is a device that measures the electrical activity of the heart, and has been widely used to obtain biopotential signals of the heart and pulmonary system. To obtain biopotential signals, ECG electrodes coupled to an ECG device are applied to the skin of a user at various locations. However, proper placement and connection of the ECG electrodes are required for obtaining correct biopotential signals. In some existing ECG devices, ECG electrodes are embedded in a soft plastic material and separated from one another by a fixed spacing. Such ECG devices are attached to either the right side or the left side of the chest due to the short fixed electrode spacing. Besides, it may be difficult to apply the ECG devices to a body portion with a particular shape or curve such as the breast portion of a female user. Moreover, noise from myoelectricity or breathing may be detected and captured by the ECG devices, resulting in distortion of ECG signals.

SUMMARY

Examples of the present invention provide a portable electrocardiography (ECG) device that includes a first pair of first type snap-in buttons at a first plane of a case. The first type snap-in buttons are configured for coupling to ECG electrodes having a second type snap-in button. The portable ECG device also includes a processor in electrical connection with the first pair of first type snap-in buttons. The processor is configured for monitoring and processing electrocardiography signals obtained by the ECG electrodes.

In some embodiments, the first type snap-in button is a female type and the second type snap-in button is a male type.

In some embodiments, the portable electrocardiography (ECG) device further includes a first pair of arms configured to be detachably coupled to the first pair of the first type snap-in buttons.

In some embodiments, the first pair of arms is pivoted at the first pair of the first type snap-in buttons and is allowed to rotate with respect to the first pair of the first type snap-in buttons.

In some embodiments, the first pair of arms includes a second type snap-in button at one end and a first type snap-in button at the other end.

In some embodiments, the second type snap-in button faces a direction opposite to that of the first type snap-in button.

In some embodiments, each of the first pair of arms further includes a bump on a backside of the first type snap-in button.

In some embodiments, the first pair of arms includes a conductive material configured to transmit the electrocardiography signals.

In some embodiments, the first pair of arms is flexible.

In some embodiments, the first pair of arms includes a flexible material with a memory feature.

In some embodiments, the portable electrocardiography (ECG) device further includes a pair of receptacles configured for storing the first pair of arms.

In some embodiments, the portable electrocardiography (ECG) device further includes a second pair of arms configured to be detachably coupled to the first pair of the arms.

In some embodiments, each of the second pair of arms includes a second type snap-in button at one end and a first type snap-in button at the other end, wherein the second type snap-in button faces a direction opposite to that of the first type snap-in button.

In some embodiments, each of the second pair of arms further includes a first type snap-in button on a backside of the second type snap-in button, wherein the first type snap-in buttons of the second pair of arms are configured for coupling to an ECG electrode having a second type snap-in button.

In some embodiments, the portable electrocardiography (ECG) device further includes a second pair of the first type snap-in buttons located at a second plane of the case.

In some embodiments, the second plane is raised above the first plane.

In some embodiments, the portable electrocardiography (ECG) device further includes a third pair of arms configured to detachably couple to the second pair of the first type snap-in buttons.

In some embodiments, each of the third pair of arms includes a second type snap-in button at one end and a first type snap-in button at the other end, wherein the second type snap-in button faces a direction opposite to that of the first type snap-in button.

In some embodiments, the processor is configured to send the electrocardiography signals in a wireless manner.

In some embodiments, the portable electrocardiography (ECG) device further includes a display configured for showing information on the electrocardiography signals.

BRIEF DESCRIPTION OF THE DRAWINGS

The invention will now be described further, by way of example, with reference to the accompanying drawings, in which: All drawings are intended to illustrate some aspects and embodiments of the present disclosure. The drawings described are only schematic and are non-limiting.

Figure 1A:
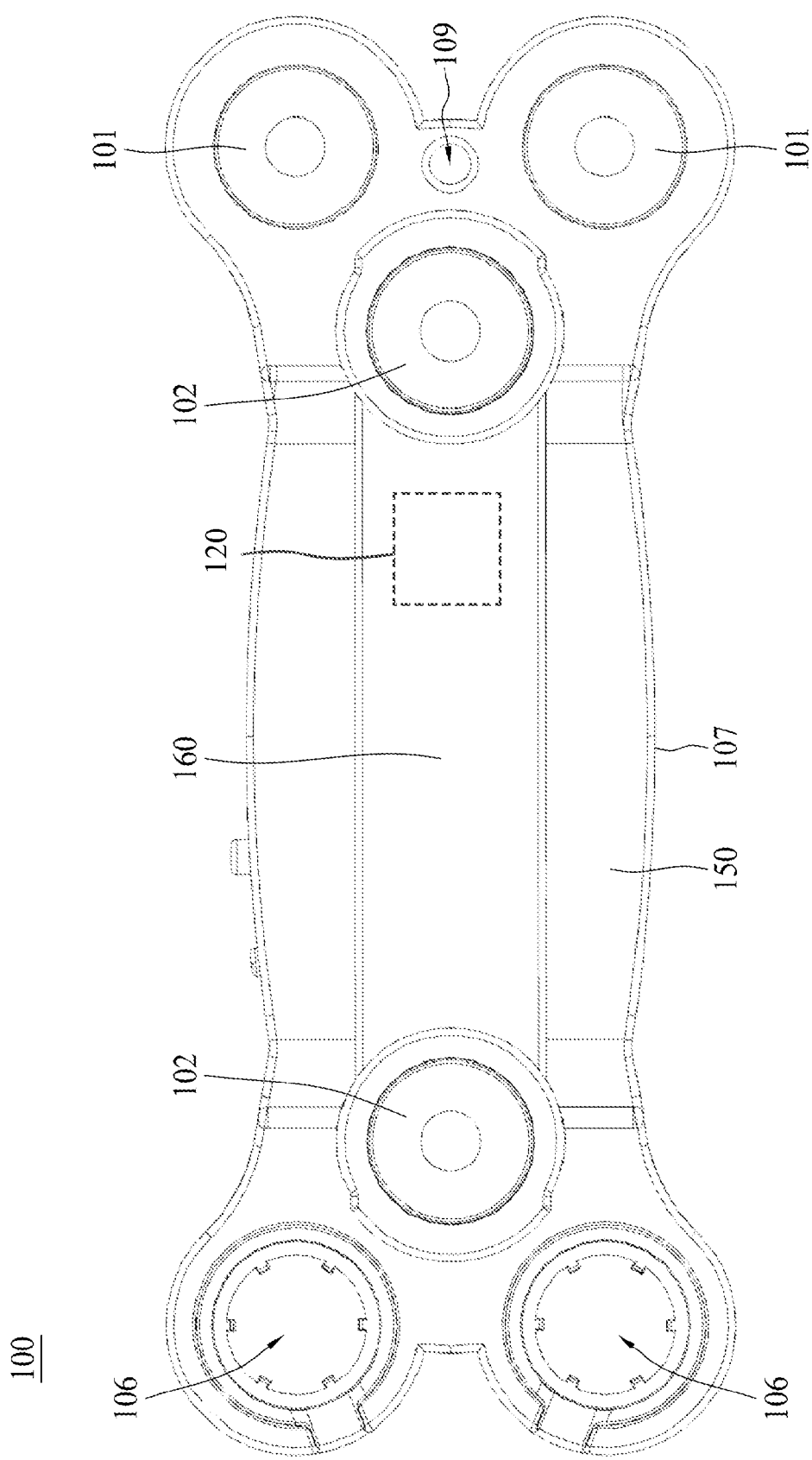
FIGS. 1A and 1B depict schematic views of a portable ECG device according to an embodiment of the present invention.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention.

Any reference signs in the claims shall not be construed as limiting the scope.

In the different drawings, the same reference signs refer to the same or analogous elements.

DESCRIPTION OF THE EMBODIMENTS

FIG. 1A is a schematic bottom view of a portable ECG device 100 according to an embodiment of the present invention. The portable ECG device 100 is configured for monitoring and processing ECG signals or other physiological signals. Specifically, the portable ECG device 100 is capable of measuring the electrical activity of the heart.

Referring to FIG. 1A, the portable ECG device 100 includes a first pair of first type snap-in buttons 101, a second pair of first type snap-in buttons 102, a pair of receptacles 106, and a case 107.

The first pair of first type snap-in buttons 101 is configured to couple with electrodes for contact with the skin of a user. In some embodiments, each of the first type snap-in buttons 101 includes a socket, which is a female button. In other embodiments, each of the first type snap-in buttons 101 includes a stud, which is a male button. Although snap-in buttons 101 are shown in a pair, other numbers of snap-in buttons 101 are within the contemplated scope of the present invention. In operation, the first pair of first type snap-in buttons 101 can be used for coupling with, by attaching to or locking in, patch-type ECG electrodes (not shown). In this embodiment, the first type snap-in buttons 101 are female buttons for locking in the ECG electrodes in the form of a second type or male button.

The case 107 includes a first plane 150 and a second plane 160 of different heights. In the present embodiment, the second plane 160 is raised above the first plane 150. The first pair of first type snap-in buttons 101 is located at the first plane 150 of the case 107. Further, the first type snap-in buttons 101 are arranged in a first direction and separated from one another by a first distance. In some embodiments, the first distance ranges from approximately 3 to 10 centimeters.

The ECG electrodes include male type snap-in buttons for electrical and mechanical connection with the first pair of first type snap-in buttons 101. The ECG electrodes also include outer release liners for protection. Once the outer release liners are removed, the ECG electrodes can be attached to the chest of a user. Moreover, the ECG electrodes have an adhesive patch to ensure a good contact with the user's skin. In addition, the ECG electrodes are disposable and reusable.

As the ECG electrodes are locked into the first pair of first type snap-in buttons 101, the portable ECG device 100 captures ECG signals such as p-waves and QRS amplitude. In some embodiments, the portable ECG device 100 captures change in capacitance amplitude between ECG electrodes, which allows a physician to check a patient's physiological status immediately.

Similarly, the second pair of first type snap-in buttons 102 may include female buttons in some embodiments, or include male buttons in other embodiments. The second pair of first type snap-in buttons 102 may be used for coupling with the patch-type ECG electrodes. Although snap-in buttons 102 are shown in a pair, other numbers of snap-in buttons 102 are within the contemplated scope of the present invention. Moreover, the second pair of first type snap-in buttons 102 is located at the second plane 160 of the case 107. Different heights of planes 150 and 160 for snap-in buttons 101 and 102 avoid mechanical interference between these snap-in elements. The second pair of first type snap-in buttons 102 is arranged in a second direction. In some embodiments, the first direction and the second direction are substantially orthogonal to each other. Furthermore, the snap-in buttons 102 are separated from each other by a second distance. In some embodiments, the second distance ranges from approximately 5 to 15 centimeters. Moreover, the first distance is shorter than the second distance so as to facilitate different measuring purposes.

In the case 107 a processor 120 is configured for monitoring and processing electrocardiography (ECG) signals. For example, the processor analyzes an ECG waveform, determines an analog electrical signal, generates an electrical waveform, and sends signals either by wire or wirelessly (e.g., via Bluetooth technology, GSM/GPRS or Wi-Fi) to a host device. A hole 109 in the case 107 may be stringed so that the portable ECG device 100 can be, for example, hung on a user's neck.

Figure 1B:
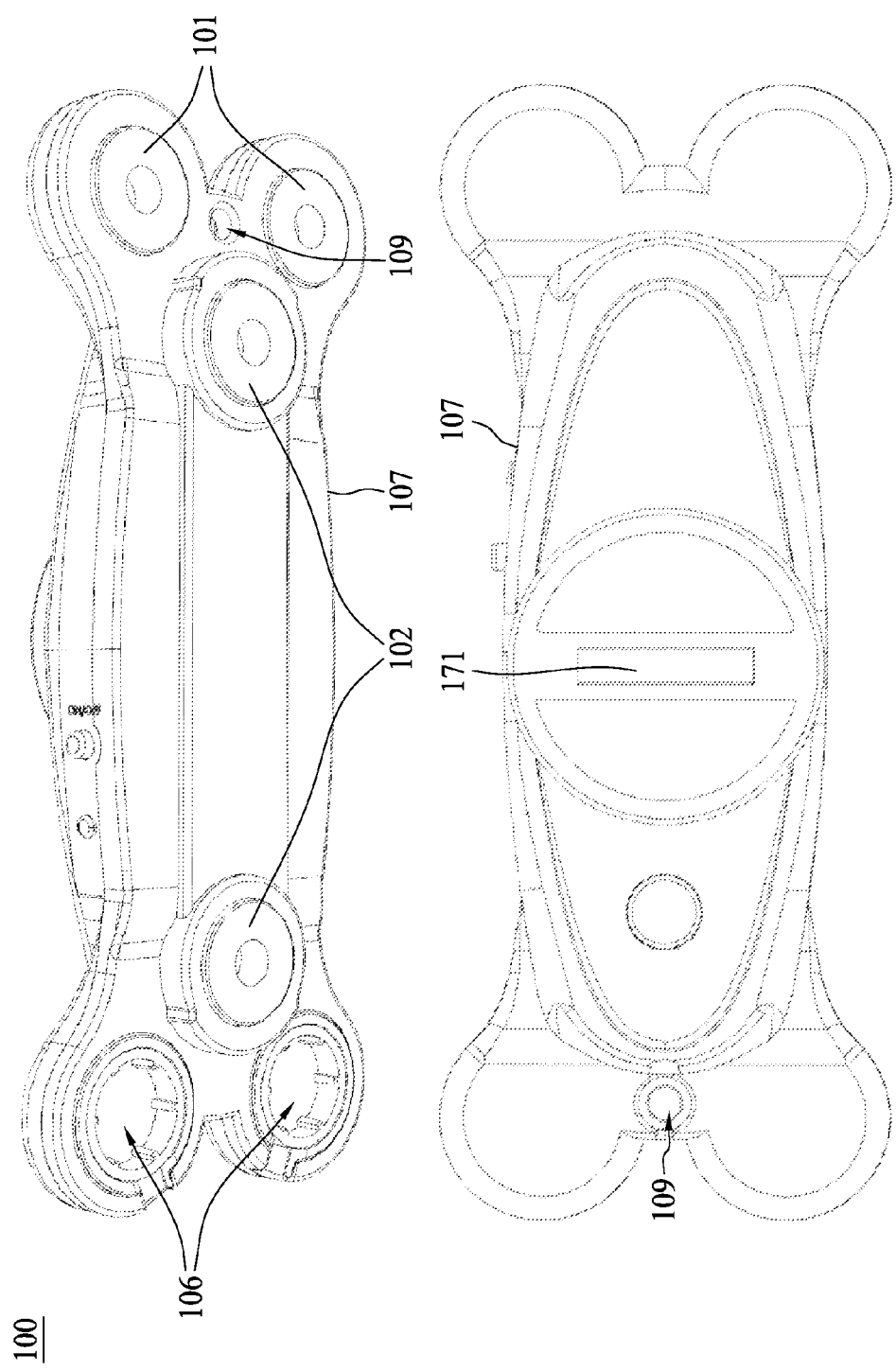

FIG. 1B depicts schematic bottom and top views of the portable ECG device 100 according to an embodiment of the present invention. The portable ECG device 100 includes a display 171 configured for showing real-time information such as electrocardiography signals, ECG waveforms, heart beat and body temperature.

Figure 2A:
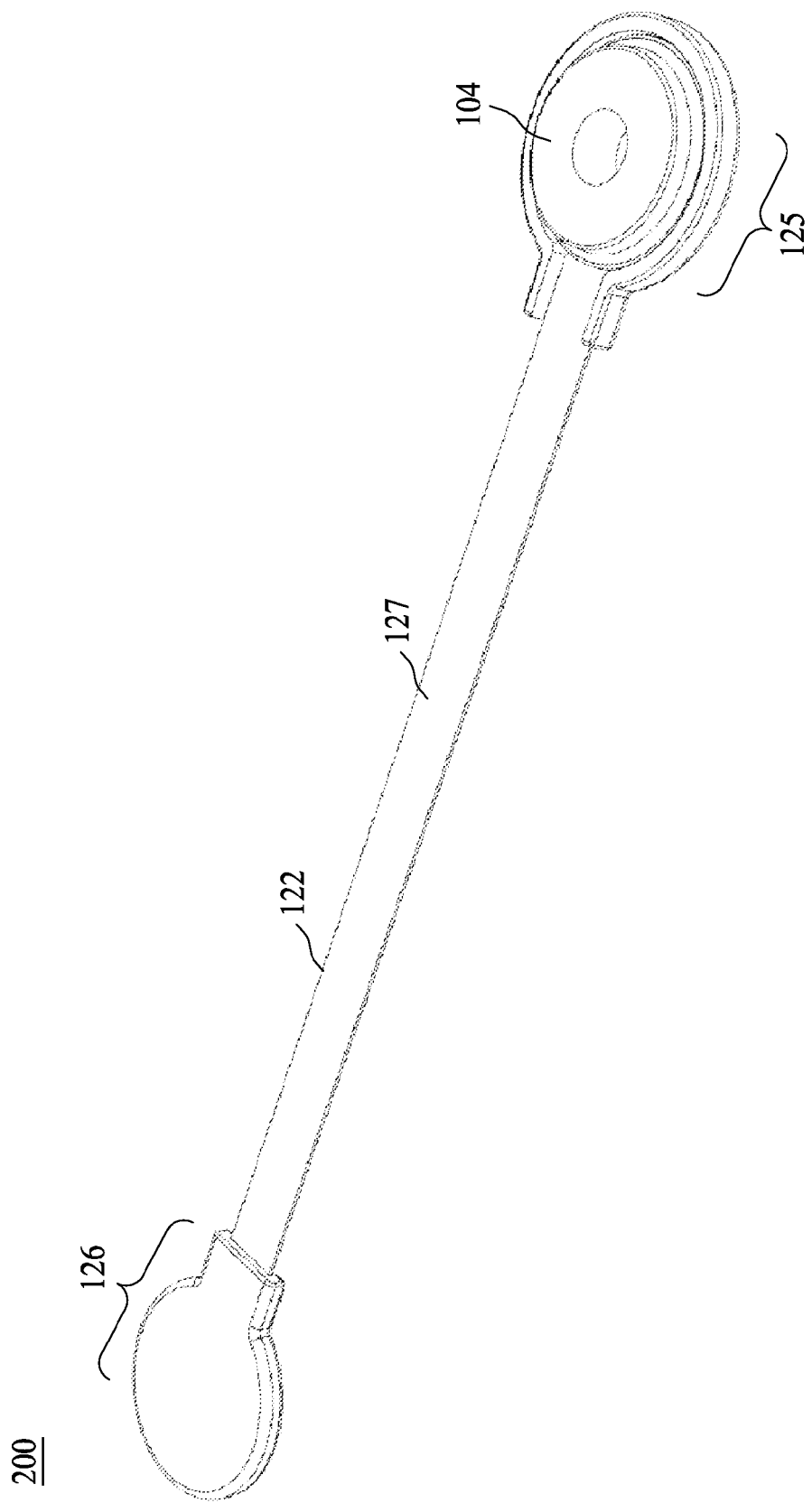
FIGS. 2A and 2B depict schematic views of an arm for a portable ECG device according to an embodiment of the present invention.
Figure 2B:
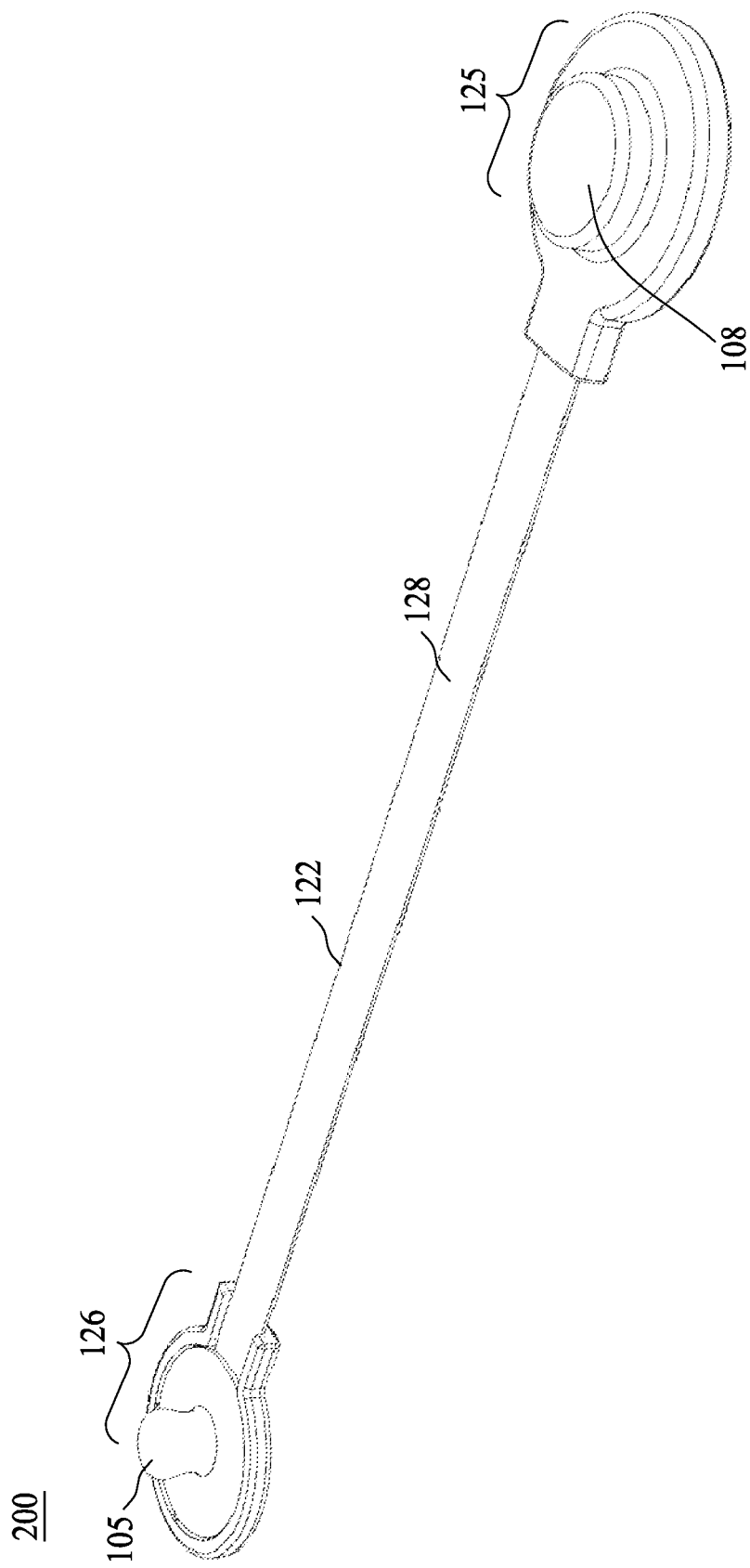

The portable ECG device 100 may further comprise or cooperate with a pair of detachable arms to obtain better and stronger ECG signals. FIGS. 2A and 2B depict schematic views of an arm 200 for a portable ECG device according to an embodiment of the present invention. Referring to FIGS. 2A and 2B, the arm 200 includes a strip 122, a first type snap-in button 104 at a first end 125, and a second type snap-in button 105 at a second end 126.

In some embodiments, the strip 122 is implemented as a thin metal sheet having a first side 127 and a second side 128. Further, the strip 122 includes a conductive material to allow the arm 200 to transmit electrocardiography signals. The conductive material can be copper, silver, stainless steel, or an alloy. In some embodiments, the strip 122 is flexible or bendable so that the arm 200 can be fit to the body shape of a user. Moreover, the strip 122 is made of a flexible material with a memory feature. With the memory feature of flexible material, the strip 122 is shaped or mould to a specific curve to fit different body shapes.

In some embodiments, the length of the strip 122 ranges from approximately 10 to 20 centimeters. Further, the length of the strip 122 may be predetermined for measuring an ECG waveform so as to facilitate proper placements of ECG electrodes. By a predetermined length of the strip 122, clinicians or patients can easily determine the position of each ECG electrodes on the skin. In addition, the predetermined length of the strip 122 enables the patients to use the portable ECG device 100 for quick and reliable ECG measurement or recording at home.

In some embodiments, an insulating layer is coated on the strip 122. The insulating layer prevents a direct contact between the conductive material and the skin. Moreover, the insulating layer prevents the strip 122 from interference.

In FIG. 2A, the first type snap-in button 104 at the first end 125 is disposed on the first side 127 of the strip 122. In FIG. 2B, the second type snap-in button 105 at the second end 126 is disposed on the second side 128 of the strip. As a result, the second type snap-in button 105 faces a direction opposite to that of the first type snap-in button 104. The second type snap-in button 105 is electrically connected to the first type snap-in button 104 by the strip 122 to allow transmission of ECG signals.

In some embodiments, the first type snap-in button 104 is movable along the strip 122. Accordingly, the position of the first type snap-in button 104 can be adjusted.

Figure 3A:
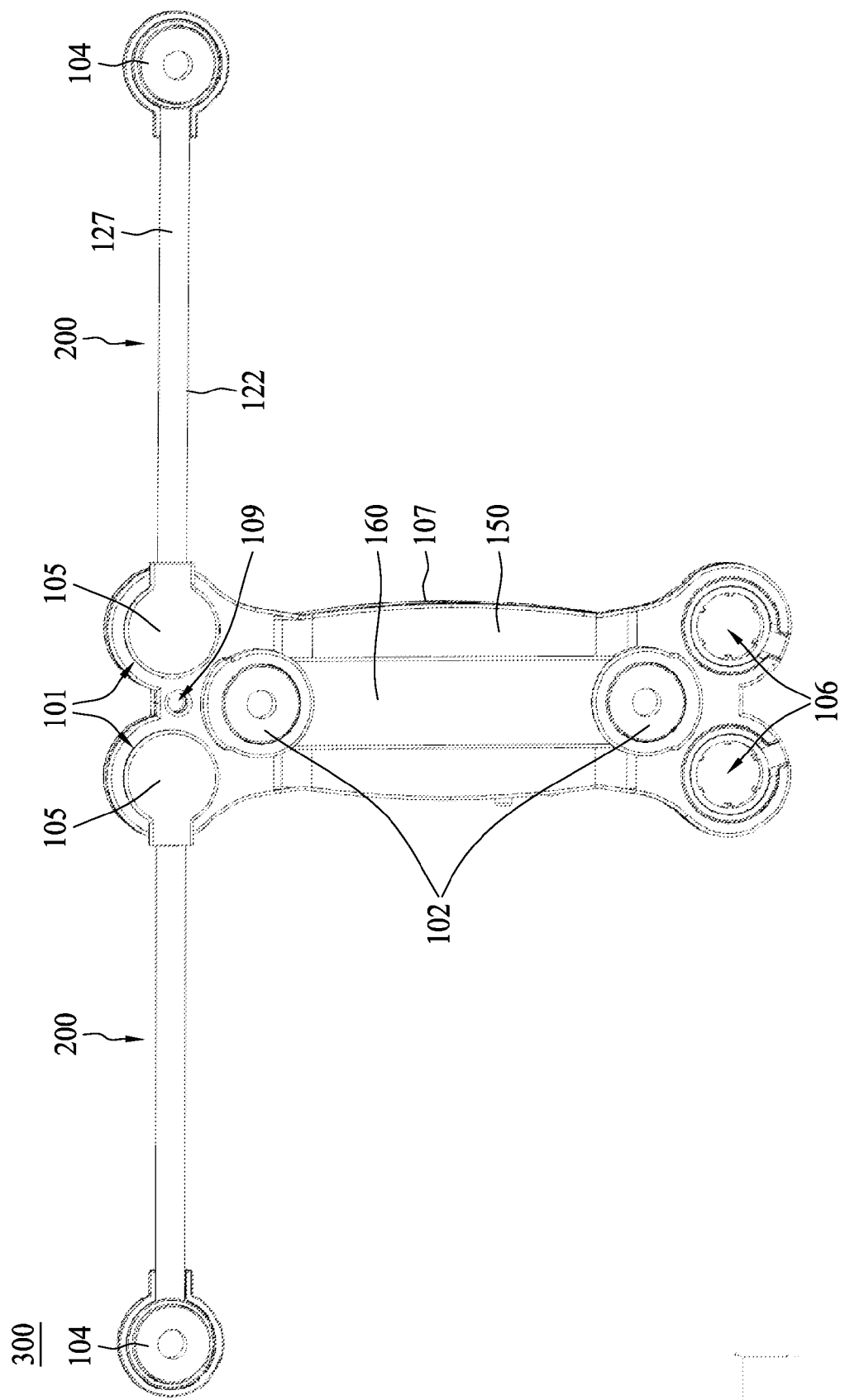
FIGS. 3A and 3B depict schematic views of a portable ECG device according to another embodiment of the present invention.

A first pair of the arms 200 can work with the portable ECG device 100, as a portable ECG device 300 shown in FIG. 3A. Specifically, the second type snap-in buttons 105 of the arms 200 lock into the first pair of first type snap-in buttons 101. The first pair of the arms 200 is pivoted at the first type snap-in buttons 101 and is electrically and mechanically connected to the portable ECG device 100. Since the second type snap-in buttons 105 of the arms 200 are pivoted at the snap-in buttons 101, the first type snap-in buttons 104 of the arms 200 are allowed to rotate with respect to the portable ECG device 100. Furthermore, the snap-in buttons 105 of the first pair of the arms 200 are detachable from the snap-in buttons 101.

Figure 3B:
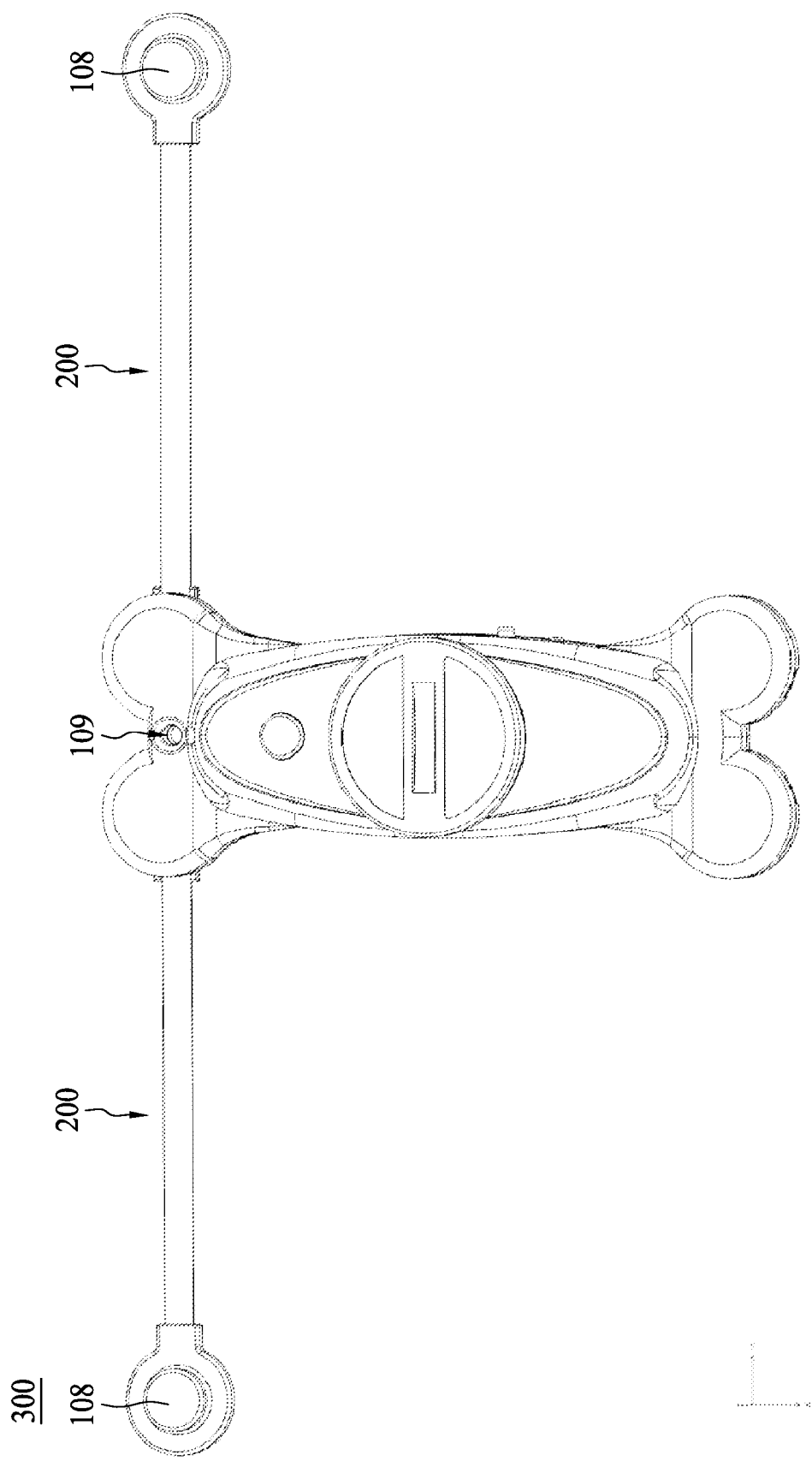

The pair of receptacles 106, located at the first plane 150 of the case 107, is configured to store the first type snap-in buttons 104 of the arms 200. A distance between the first type snap-in buttons 101 and the receptacles 106 is substantially the same as the length of the first pair of the arms 200. Effectively, the pair of receptacles 106 receives the first type snap-in buttons 104 as the second type snap-in buttons 105 are coupled to the first type snap-in buttons 101, thereby storing the arms 200 in the case 107 of the portable ECG device 100. The first type snap-in buttons 104 include bumps 108 (FIG. 3B) to fit to the receptacles 106. The bump 108 is located on a backside of the first type snap-in button 104.

In operation, ECG electrodes having a second type snap-in button are locked into the first type snap-in buttons 104. As the ECG electrodes are attached to the portable ECG device 300, the portable ECG device 300 is capable of measuring electrical activity of the heart. Besides, the ECG electrodes are adhesive patches so that the portable ECG device 300 can be attached to a human skin. The ECG signals monitored and detected by the ECG electrodes are processed and transmitted to a host device by the processor in the case 107.

The first pair of the arms 200 provides adjustable spacing for the ECG electrodes. As a result, the spacing of the ECG electrodes can be large enough so that noise from myoelectricity and breathing is reduced. Effectively, the portable ECG device 300 is able to capture a stronger and more correct ECG signal.

Figure 4:
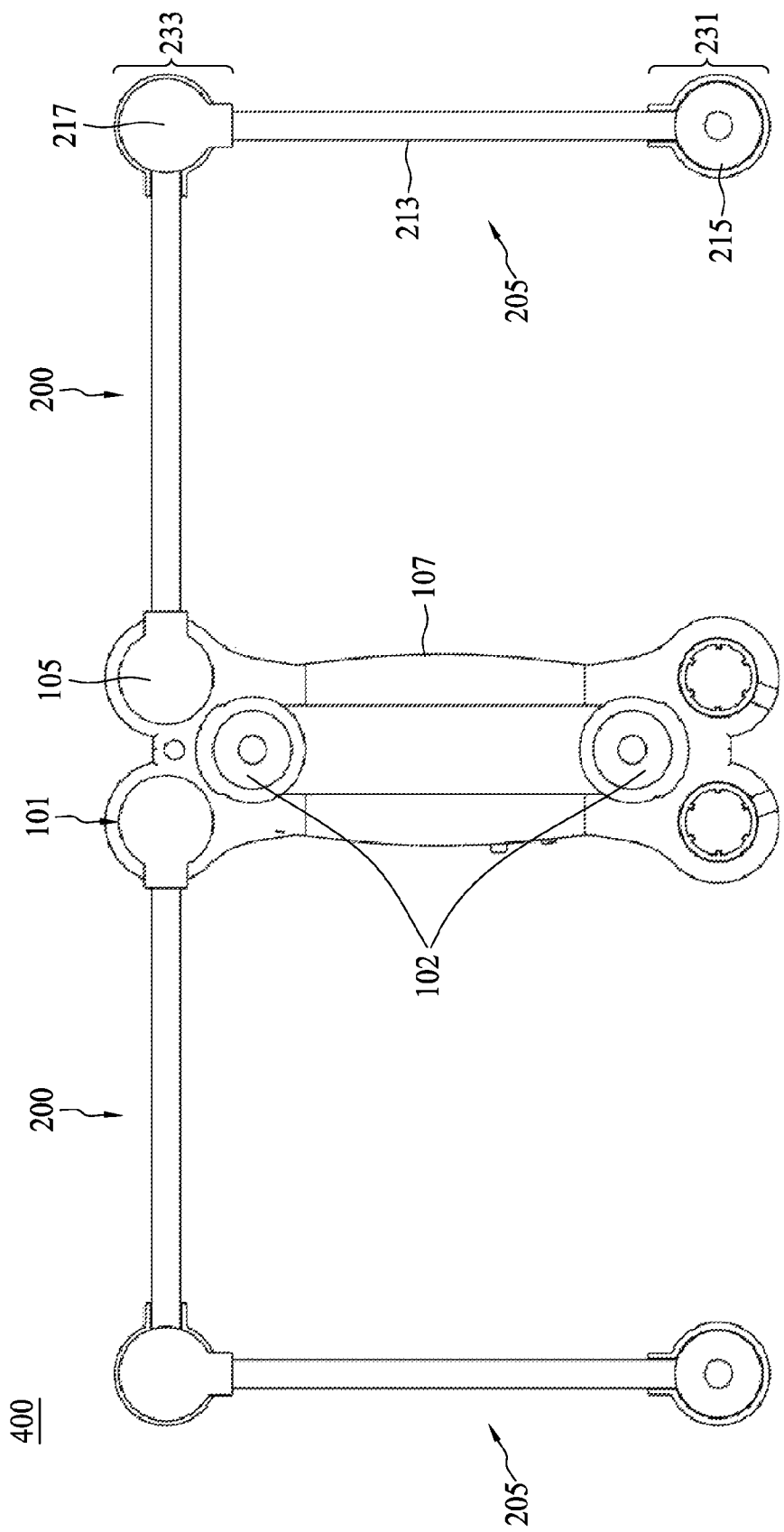
FIG. 4 depicts a schematic view of a portable ECG device according to still another embodiment of the present invention.

FIG. 4 depicts a schematic view of a portable ECG device 400 according to an embodiment of the present invention. The portable ECG device 400 is similar to the portable ECG device 300 described and illustrated with respect to FIGS. 3A and 3B except that, for example, a second pair of arms 205 is provided. The second pair of arms 205 is detachably coupled to the first pair of arms 200. The second pair of the arms 205 has substantially the same structure as the first pair of arms 200. Each of the arms 205 includes a strip 213, a first type snap-in button 215, and a second type snap-in button 217. The first type snap-in button 215 is located on a first end 231, and the second type snap-in button 217 is located on a second end 233.

In operation, the second type snap-in button 217 is locked into the first type snap-in button 104. Thus, the second pair of arms 205 is pivoted at the first type snap-in button 104. With the first pair of arms 200 and the second pair of arms 205, the portable ECG device 400 has a wider range of measurement than the portable ECG device 300. Effectively, the portable ECG device 400 is capable of measuring ECG signals in some specific vectors. In addition, a larger space between the ECG electrodes contributes to a stronger and clearer ECG waveform.

In some embodiments, the second pair of arms 205 further includes a first type snap-in button (not shown) on the backside of the second type snap-in button 217. The first type snap-in buttons are configured for locking in an ECG electrode having a second type snap-in button. As such, the portable ECG device 400 has at least six ECG electrodes, including the second pair of the first type snap-in buttons 102, a pair of the first type snap-in button 215, and additionally a pair of first type snap-in button on the backside of the second type snap-in button 217 for a multi-point measurement. In some embodiments, more arms are connected to each other to provide more snap-in buttons for ECG electrodes.

Figure 5:
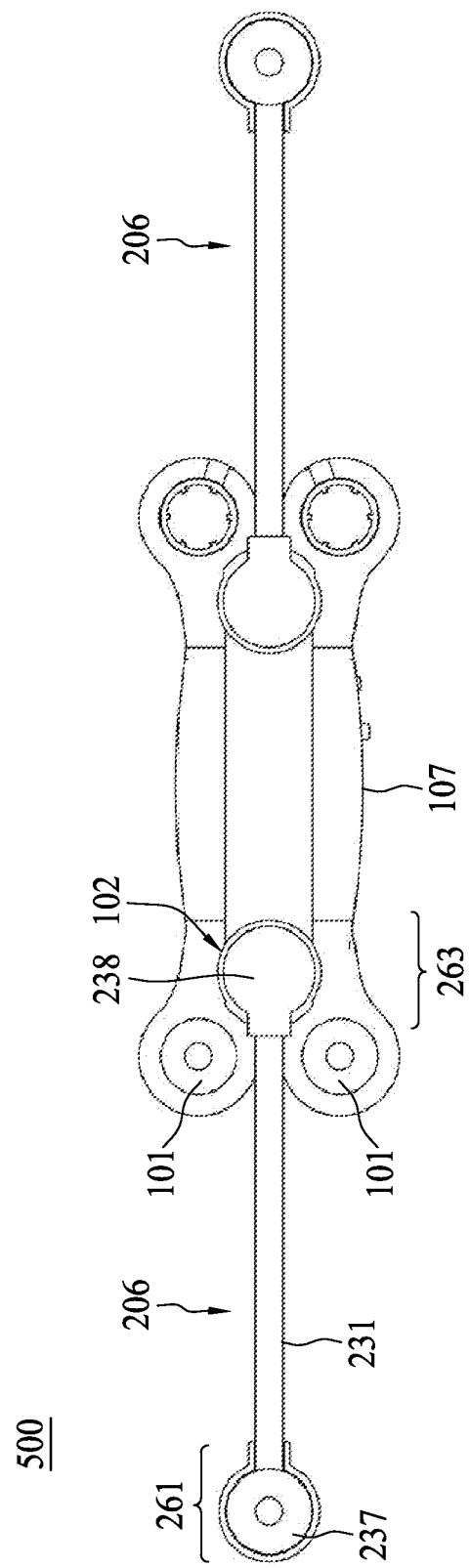
FIG. 5 depicts a schematic view of a portable ECG device according to yet another embodiment of the present invention.

FIG. 5 depicts a schematic view of a portable ECG device 500 according to an embodiment of the present invention. Referring to FIG. 5, the portable ECG device 500 is similar to the portable ECG device 100 described and illustrated with respect to FIGS. 1A and 1B except that, for example, a third pair of arms 206 is provided. The third pair of arms 206 has the same structure as the first pair of arms 200. Moreover, the third pair of arms 206 is detachably coupled to the second pair of the first type snap-in buttons 102 and is pivoted and rotatable with respect to the snap-in buttons 102. Each of the arms 206 includes a strip 231, a first type snap-in button 237, and a second type snap-in button 238. The first type snap-in button 237 is located on a first end 261, and the second type snap-in button 238 is located on a second end 263.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A portable electrocardiography (ECG) device comprising:
    a case including at least a first side and an opposing second side;
    a first pair of first type snap-in buttons on a first plane defined by the first side of the case;
    a second pair of first type snap-in buttons on a second plane defined by the first side of the case, wherein the first plane and the second plane are different but parallel to one another, and wherein each first type snap-in button is configured for coupling to an ECG electrode or an arm having a second type snap-in button;

a processor in electrical connection with each first type snap-in button in the first pair of first type snap-in buttons, wherein the processor is configured for monitoring and processing process ECG signals obtained by ECG electrodes; and a display on the second side of the case, wherein the display is configured for showing information indicative of the ECG signals, and wherein the processor is disposed within the case.

2. The portable ECG device of claim 1, wherein the first type snap-in buttons are female type snap-in buttons, and wherein the second type snap-in buttons are male type snap-in buttons.

3. The portable ECG device of claim 1 further comprising a first pair of arms configured to be detachably coupled to the first pair of first type snap-in buttons.

4. The portable ECG device of claim 3, wherein each arm in the first pair of arms is configured to (i) pivot at and (ii) rotate with respect to one of the first type snap-in buttons included in the first pair of first type snap-in buttons.

5. The portable ECG device of claim 4, wherein each arm in the first pair of arms comprises a second type snap-in button at one end of the arm and a first type snap-in button at an opposite end of the arm.

6. The portable ECG device of claim 5, wherein, on each arm in the first pair of arms, the second type snap-in button faces a direction opposite to that of the first type snap-in button.

7. The portable ECG device of claim 6, wherein each arm in the first pair of arms further comprises a bump on an opposite side of the end of the arm at which the first type snap-in button is located.

8. The portable ECG device of claim 7, wherein each arm in the first pair of arms comprises a conductive material configured to transmit the ECG signals.

9. The portable ECG device of claim 8, wherein each arm in the first pair of arms is flexible and has a memory feature.

10. The portable ECG device of claim 7 further comprising a pair of receptacles configured for securing the first pair of arms to the case, wherein the pair of receptacles are spaced apart from the first pair of first type snap-in buttons and are on the first plane of the case, and wherein each receptacle is configured to detachably couple with the bump of a respective arm.

11. The portable ECG device of claim 3 further comprising a second pair of arms configured to be detachably coupled to the first pair of the arms.

12. The portable ECG device of claim 11, wherein each arm in the second pair of arms comprises a second type snap-in button at one end and a first type snap-in button at an opposite end, wherein the second type snap-in button faces a direction opposite to that of the first type snap-in button.

13. The portable ECG device of claim 12, wherein each arm in the second pair of arms further comprises an additional first type snap-in button on an opposite side of the end of the arm at which the second type snap-in button is located, wherein the additional first type snap-in button of each arm in the second pair of arms is configured for coupling to an ECG electrode having a second type snap-in button.

14. The portable ECG device of claim 13 further comprising a third pair of arms configured to detachably couple to the second pair of first type snap-in buttons.

15. The portable ECG device of claim 14, wherein each arm in the third pair of arms comprises a second type snap-in button at one end of the arm and a first type snap-in button at an opposite end of the arm, and wherein, for each arm in the third pair of arms, the second type snap-in button faces a direction opposite to that of the first type snap-in button.

16. A portable electrocardiography (ECG) device comprising:

a case including at least a first side and an opposing second side;

a first pair of first type snap-in buttons on a first plane defined by the first side of the case, wherein each first type snap-in button is configured to couple to an ECG electrode or to a second type snap-in button;

a second pair of first type snap-in buttons on a second plane defined by the first side of the case, wherein the first pair of first type snap-in buttons is arranged in a first direction, the second pair of first type snap-in buttons is arranged in a second direction, and the first direction is orthogonal to the second direction;

a pair of arms, each arm of the pair of arms comprising:
 a first end and a distal second end;
 a first type snap-in button at the first end;
 a second type snap-in button at the second end, wherein the second type snap-in button faces a direction opposite to that of the first type snap-in button at the first end, and is configured for coupling to one of the first type snap-in buttons in the first pair of first type snap-in buttons on the case; and
 a bump at the first end and on an opposite side of the arm from the first type snap-in button;
 wherein each arm in the first pair of arms is configured to pivot at and rotate with respect to one of the first type snap-in buttons included in the first pair of first type snap-in buttons on the case;

a pair of receptacles on the first plane of the case, wherein the receptacles are configured for detachably securing the first pair of arms to the case by coupling to the bumps on the arms;

a processor within the case that is configured to be electrically coupled with each first type snap-in button, wherein the processor is configured for monitoring and processing process ECG signals obtained by one or more ECG electrodes coupled to at least one of the first type snap-in buttons on the case or on the arms; and a display on the second side of the case, wherein the display is configured for showing information indicative of the ECG signals.

* * * * *